US00PP15152P2

(12) United States Plant Patent
Holland

(10) Patent No.: US PP15,152 P2
(45) Date of Patent: Sep. 21, 2004

(54) LILAC PLANT NAMED 'BAILDUST'

(50) Latin Name: *Syringa hybrida*
Varietal Denomination: cv. Baildust

(75) Inventor: Neal S. Holland, Harwood, ND (US)

(73) Assignee: Bailey Nurseries, Inc., St. Paul, MN (US)

( * ) Notice: Subject to any disclaimer, the term of this patent is extended or adjusted under 35 U.S.C. 154(b) by 0 days.

(21) Appl. No.: 10/158,047

(22) Filed: May 31, 2002

(51) Int. Cl.[7] ..... A01H 5/00
(52) U.S. Cl. ..... Plt./248
(58) Field of Search ..... Plt./248

*Primary Examiner*—Bruce R. Campell
*Assistant Examiner*—Michelle Kizilkaya
(74) *Attorney, Agent, or Firm*—Burns, Doane, Swecker & Mathis, L.L.P.

(57) ABSTRACT

A new and distinct highly ornamental cultivar of *Syringa meyeri*×*Syringa microphylla* is provided. A Lilac plant having a rounded neat compact growth habit is described. Highly attractive trusses of fragrant pale antique pink blossoms are formed in late spring and sometimes also during late summer. Good winter hardiness is made possible and the plant has been found to be relatively free of insect and disease problems during observations to date. The plant is particularly well-suited for growing as an ornamental specimen or as a mass planting in the landscape.

2 Drawing Sheets

Figure 1:
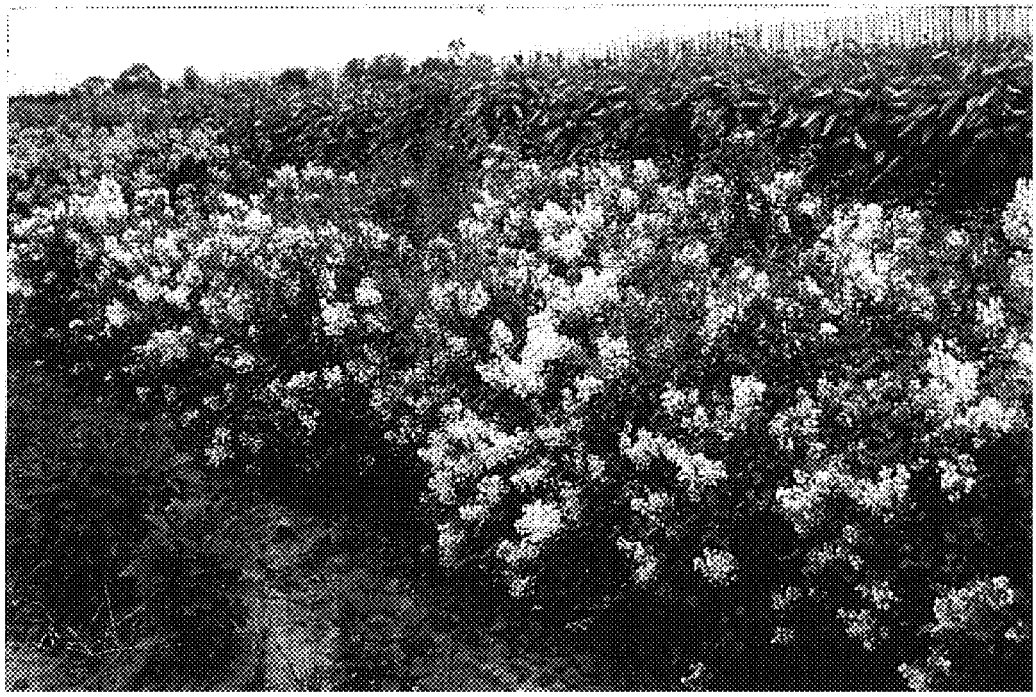

Botanical commercial classification: Syringa hybrida/Lilac Shrub.
Varietal denomination: cv. 'Baildust'.

SUMMARY OF THE INVENTION

The new Lilac plant of the present invention was created at Harwood, N. Dak., by the cross of *Syringa meyeri* 'Palibin' (non-patented in the United States) and *Syringa microphylla* 'Superba' (non-patented in the United States). The parentage can be summarized as follows:

'Palibin'×'Superba'.

Seeds from the cross were collected during 1976, were planted, and the resulting plants were observed. A single plant of new cultivar was selected during 1985 in view of its distinctive combination of ornamental characteristics. This plant initially was designated No. 85-4.

It was found that the cultivar of *Syringa meyeri*×*Syringa microphylla* exhibits the following combination of characteristics:

(a) exhibits a rounded neat compact growth habit, (b) forms attractive trusses of fragrant pale antique pink blossoms in late spring and sometimes also during late summer, (c) is relatively free of insect and disease problems, and (d) is well-suited for growing as a distinctive ornamental shrub in the landscape.

The new cultivar of the present invention provides a distinctive antique pink blossom coloration to the landscape that is displayed in late spring after many other shrubs have finished flowering. The pink blossoms upon maturity fade to almost white. The new cultivar will sometimes repeat bloom during late summer to provide further ornamentation; however, not as many blossoms are then formed as in late spring. It can be grown to advantage as a specimen shrub or in a mass planting. The plant is versatile for many uses in the landscape including foundation plantings and informal hedges. The superior hardiness of the *Syringa meyeri* 'Palibin' parent which generally is lacking in the *Syringa microphylla* 'Superba' parent is imparted to the new cultivar of the present invention. However, some winter injury has been observed under wet conditions.

The new cultivar can be readily distinguished from the 'Bailbelle' cultivar (U.S. Plant Pat. No. 12,294) that was the product of the same cross. More specifically, the blossoms of the 'Bailbelle' cultivar are a distinctive wine-red while those of the new cultivar of the present invention are pale antique pink. The new cultivar also is slightly more upright.

The new cultivar of the present invention was asexually propagated by the use of rooted cuttings and grafting at St. Paul, Minn., during 1992, and the progeny were field planted during 1993. The distinctive characteristics of the new cultivar have been found to be stable and to be capable of transmission from one generation to another following such asexual propagation at St. Paul, Minn. and elsewhere.

The new cultivar of the present invention also has been grafted on *Syringa reticulata* to form distinctive small grafted trees.

The new cultivar of the present invention has been named 'Baildust'. It is a member of the FAIRYTALE™ Series of Lilac plants that includes the 'Bailbelle' cultivar, and is being marketed under the FAIRY DUST trademark.

BRIEF DESCRIPTION OF THE PHOTOGRAPHS

The accompanying photographs show, as true as reasonably possible to make the same in color illustrations of this character typical plants of the new cultivar. The plants were propagated by use of rooted cuttings and were photographed when approximately three years of age while growing outdoors during late spring in the field at St. Paul, Minn.

FIG. 1—shows a mass planting of blossoming plants wherein the neat rounded and compact growth habit of the new cultivar is exhibited.

Figure 2:
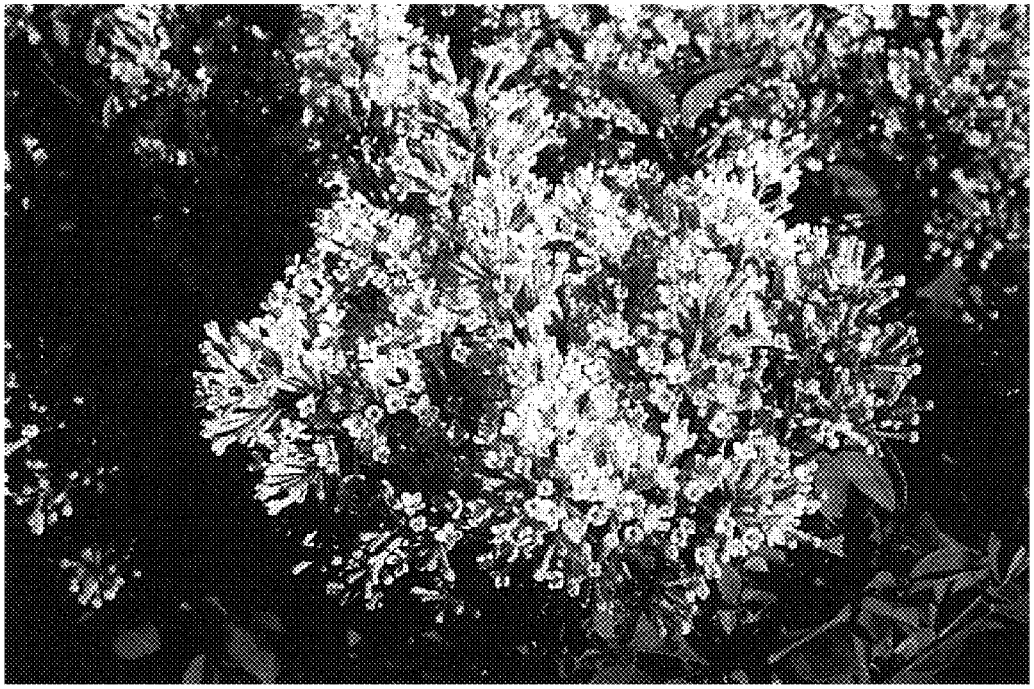

FIG. 2—shows a closer view of a truss of the antique pink buds and blossoms as well as some foliage.

Figure 3:
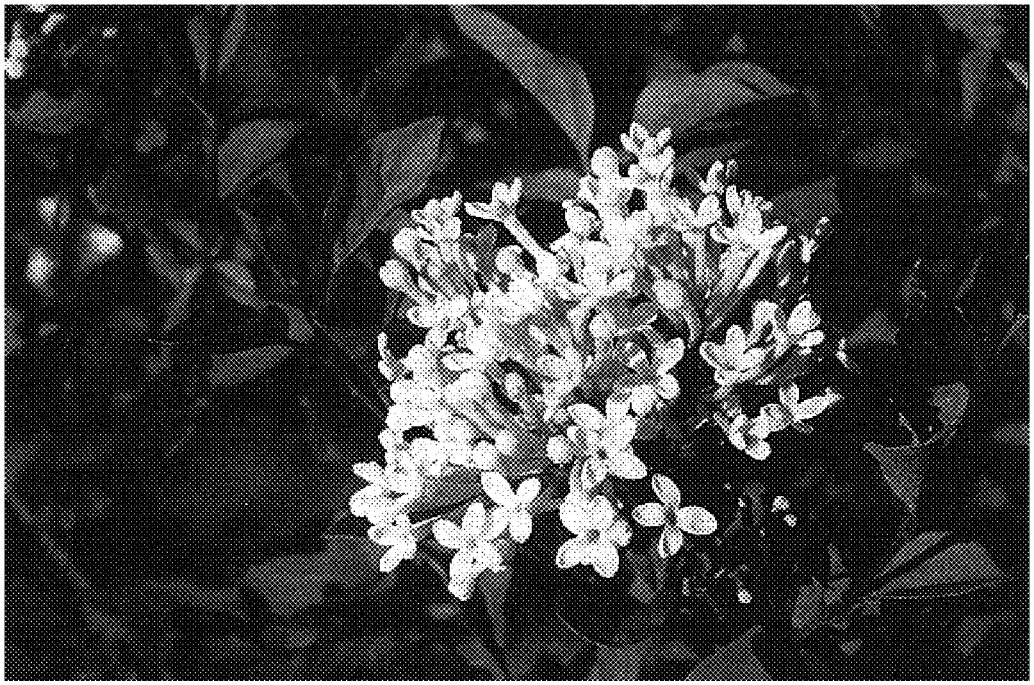

FIG. 3—shows a close-up view of the largely open pink antique blossoms with attractive foliage.

DETAILED DESCRIPTION

The chart used in the identification of colors is The R.H.S. Colour Chart of The Royal Horticultural Society, London. Common terms are to be accorded their ordinary dictionary significance. The description is based upon the observation of three year-old plants propagated by the use of rooted cuttings and growing in the field at St. Paul, Minn.

Botanical classification: *Syringa meyeri*×*Syringa microphylla*, cv. 'Baildust'.

Plant:

*Growth habit.*—Compact upright rounded shrub, and more upright than the *Syringa meyeri*, 'Palibin' parent, and slightly more upright than the 'Bailbelle' cultivar.

*Size.*—Forms a shrub of approximately 5 to 6 feet in height and width.

Bark:

*Texture.*—Glabrous.

*Color.*—Greyed-Green Group 197A.

Foliage:

*Leaf shape.*—Elliptic/ovate.

*Arrangement.*—Opposite.

*Leaf apex.*—Acute to obtuse.

*Leaf base.*—Rounded.

*Leaf margins.*—Entire.

*Color.*—Medium green, Green Group 138B (upper surface) and Green Group 138C (under surface) for young foliage, and Green Group 138A (upper surface) and 138C (under surface) for adult foliage. This can be compared to Green Group 139A (upper surface) for the adult foliage of the *Syringa meyeri* 'Palibin' parent, and Green Group 137A (upper surface) and Green Group 138C (under surface) for the adult foliage of the 'Bailbelle' cultivar.

*Petioles.*—Green Group 138B on the upper surface and Green Group 139C on the under surface.

*Stems.*—Green Group 138B (upper surface) and Greyed-Green Group 191B (under surface) of young stems, and Green Group 139C (upper surface) and Greyed-Green Group 197D (under surface) on adult wood.

*Lenticels.*—Commonly are present on stems and measure approximately 0.1 to 0.3 cm, and are Grey-Brown Group 199D in coloration.

Inflorescence:

*Arrangement.*—Opposite.

*Buds.*—In trusses, Spirea Red, Red-Purple Group 63C (upper surface) and Red-Purple Group 65C (under surface) when first appear and then fade with lightening coloration. The length commonly is 1.5 to 1.75 cm and width is approximately 0.5 cm on average.

*Flower arrangement.*—Densely packed in panicles approximately 8 to 10 cm in length and approximately 5.5 to 6 cm in width.

*Flower configuration.*—Tubular with four petal lobes at the end (as illustrated).

*Flower size.*—Approximately 0.8 to 1.4 cm in length and 0.2 to 0.5 cm in diameter at the widest point.

*Flower color.*—When first opening the petals are near Red-Purple Group 63C (upper surface) and near Red-Purple Group 65B (under surface). When blooming the petals are Red-Purple Group 65A (upper surface) and Red-Purple Group 65D (under surface). At the end of blooming the petals are near White Group 155D with highlights of Red-Purple Group 65B (upper surface) and near White Group 155D with highlights of Red-Purple Group 65D (under surface).

*Stamens.*—Two per floret, and near Red-Purple Group 65D with some near White Group 155D in coloration.

*Filaments.*—Red-Purple Group 62D in coloration.

*Anthers.*—Red-Purple Group 63B in coloration.

*Pistil.*—Approximately 0.3 cm in length.

*Style.*—Red-Purple Group 62D in coloration.

*Stigma.*—Yellow-Green Group 150D in the absence of pollen and Yellow-Green Group 154D with pollen.

*Calyx.*—Cup-shaped with an entire lobe, rugose, approximately 0.2 cm in size, initially Yellow-Green Group 145D in coloration and changing with maturity to Red-Purple Group 63B with highlights of Red-Purple Group 63C.

*Fragrance.*—Spicy lilac.

*Flowering time.*—Late spring and sometimes repeat blooms in late summer. When repeat blooming occurs there commonly are a lesser number of blooms than in late spring. However, when such blooming occurs attractive added ornamentation is provided.

*Flower duration.*—Approximately 5 to 7 days on the plant.

Hardiness: Can be grown in U.S.D.A. Hardiness Zone Nos. 3 to 7. Withstands the winter damage experienced by its *Syringa microphylla* parent which commonly is not reliably hardy in many areas. It has survived winters well during 1976 to 1993 at Harwood., N. Dak. which is on the border between U.S.D.A. Zone Nos. 3B and 4A. It also generally has wintered well when tested at St. Paul, Minn.; however, there was some winter injury at such location under wet conditions. In contrast the *Syringa microphylla* parent is considered to be hardy in U.S.D.A. Zone No. 5, and cannot winter successfully in the St. Paul, Minn., area over an extended period of time.

Culture: Similar to the Dwarf Korean Lilac. Prefers well-drained soil and a sunny growing location. Generally does not well tolerate poorly drained growing conditions.

Disease/pest resistance: Has proven to be relatively free of disease and insect problems during observations to date.

Landscape usage: Provides a hardy highly ornamental fragrant shrub having a distinctive blossom coloration that can be grown as a specimen plant or in a mass planting. Can be grown as a foundation planting or as an informal hedge.

I claim:

1. A new and distinct *Syringa meyeri*×*Syringa microphylla* plant having the following combination of characteristics:

(a) exhibits a rounded neat compact growth habit, (b) forms attractive trusses of fragrant pale antique pink blossoms in late spring and sometimes also during late summer, (c) is relatively free of insect and disease problems, and (d) is well-suited for growing as a distinctive ornamental shrub in the landscape;

substantially as illustrated and described.

* * * * *